United States Patent [19]  [11] 4,181,610
Shintani et al.  [45] Jan. 1, 1980

[54] BLOOD LEAK DETECTOR SUITABLE FOR USE WITH ARTIFICIAL KIDNEYS

[75] Inventors: Motoaki Shintani, Minoo; Yoshikazu Wada, Hirakata; Hideo Nakamachi, Kawanishi; Masao Nishikawa, Nagaokakyo; Akira Ouchida, Kawanishi, all of Japan

[73] Assignee: Takeda Chemical Industries, Ltd., Osaka, Japan

[21] Appl. No.: 703,628

[22] Filed: Jul. 8, 1976

[30] Foreign Application Priority Data

Jul. 14, 1975 [JP] Japan ................................. 50-86579

[51] Int. Cl.² ............................................. B01D 31/00
[52] U.S. Cl. .................................. 210/85; 128/214 E; 210/96.2; 210/321 B; 356/39
[58] Field of Search .................. 128/214 E, 2 L, 2 G, 128/DIG. 3, DIG. 13, 2 R; 356/40, 41, 189, 181, 51, 246, 39; 210/96 M, 34 B, 85, 87; 200/227; 300/96 B, 96 C

[56] References Cited

U.S. PATENT DOCUMENTS 3,847,483 11/1974 Shaw et al. ............................ 356/41
3,878,095 4/1975 Frasier et al. ................. 210/321 B X Primary Examiner—Frank A. Spear, Jr.
Attorney, Agent, or Firm—J. Harold Nissen

[57] ABSTRACT

A high sensitive and stable blood leak detector suitable for use with artificial kidneys. The detector has an optical portion comprising a measurement cell through which dialysis solution under test passes, an alternately energized pair of light-emitting diodes positioned on one side of the cell, and a photo sensitive detector positioned at the opposite side of the cell and close thereto. One light-emitting diode emits radiation at longer wavelengths, and the other at shorter wavelengths. Both the diodes are adjusted to produce photo detecting signals at the same level when no blood exists in the cell. The photo detecting signals at the photosensitive detector are detected and analyzed to give signals deflected in one direction in proportion to the degree of blood leak when it has occurred. When bubbles are detected, they give signals in the opposite direction, based on the fact that blood absorbs light mainly at shorter wavelengths while bubbles scatter light mainly at longer wavelengths.

11 Claims, 12 Drawing Figures

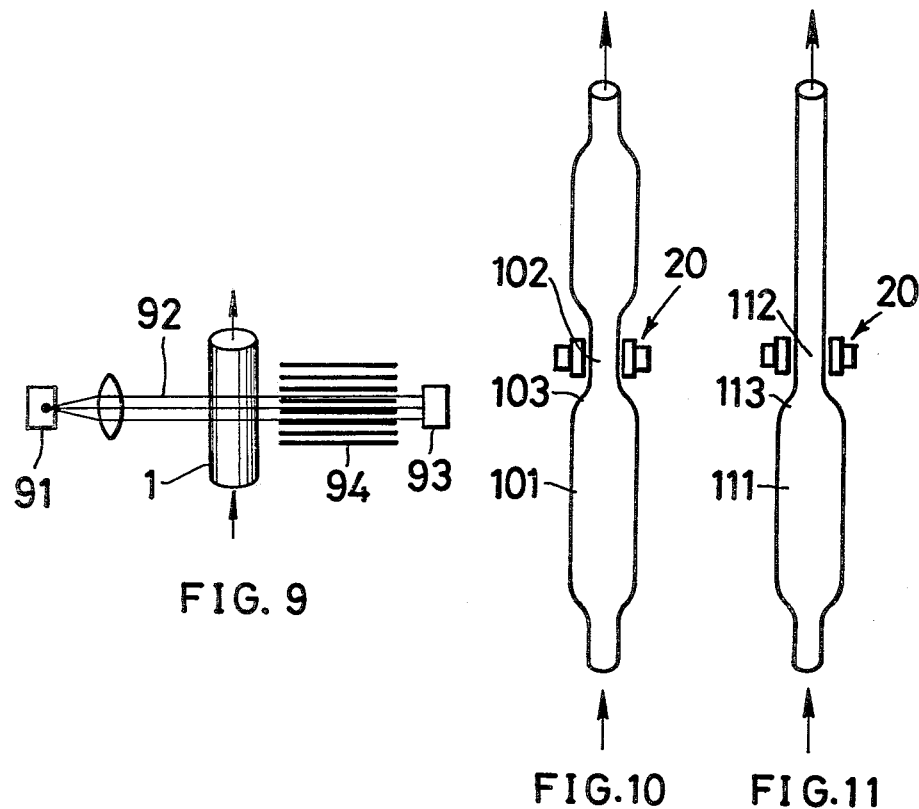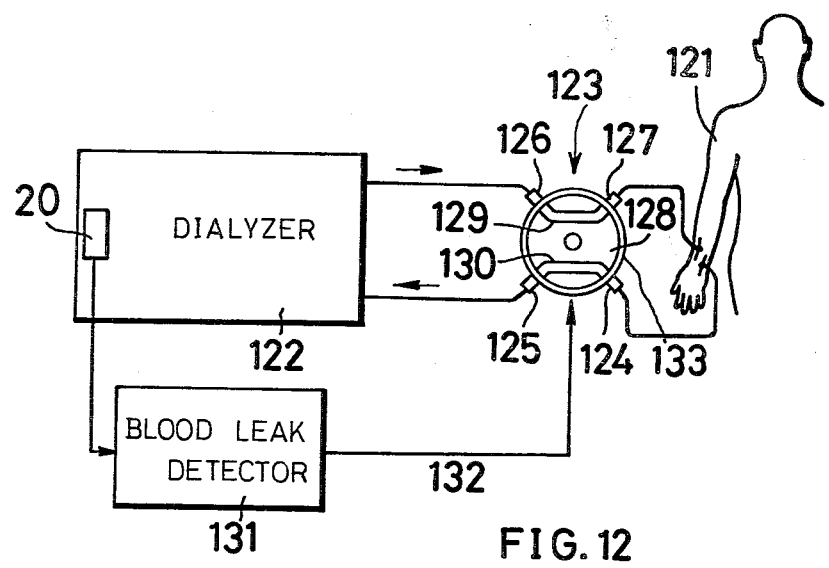

BLOOD LEAK DETECTOR SUITABLE FOR USE WITH ARTIFICIAL KIDNEYS

BACKGROUND OF THE INVENTION

This invention relates to a device for detecting a trace of blood or blood pigment, and more particularly to a blood leak detector suited for use coupled with artificial kidneys.

U.S. Pat. Nos. 3,647,299 and 3,847,483, and Japanese Patent Disclosure No. 49-15493 disclose oximeters taking advantage of a principle that blood absorbs light. The blood leak detector of this invention also employs the same principle. However, while oximeters measure blood in blood vessels of a portion of the human body, for example, an ear, blood leak detectors should promptly detect small traces of blood in a measurement cell if it should occur. Hence, blood leak detectors essentially differ from oximeters.

Japanese Patent Disclosure No. 48-46193 discloses a blood leak detector coupled with an artificial kidney. This prior art blood leak detector has two photo detecting elements, each provided with a filter of a separate color characteristic, and since each signal from the respective photo detecting element is DC amplified by a separate circuit system, this prior detector is apt to be unsuitable due to such factors as difference in circuit characteristic, leakage light from the outside, level drift due to temperature fluctuation and others. As a result, such a prior art blood detecting system is neither sufficiently stable nor highly sensitive.

Blood leak detectors must be capable of detecting blood of very low concentration, diluted with a great quantity of dialysis solution, because blood is naturally so precious to a patient under medical treatment utilizing artificial kidneys, that even such a small trace of blood as 5 ml cannot be overlooked. More particularly, since many dialyzers in actual use today require about 200 l of dialysis solution, blood leak detectors should be able to detect blood of a concentration smaller than 0.0025% of 5 ml if blood leak due to, for instance, the existence of a defective junction of dialysis membrane is to be detected. Besides, blood leak detectors must of course operate stably for many hours. Another shortcoming of such prior art blood leak detectors to be noted is that bubbles in dialysis solution are often taken for blood leak erroneously.

STATEMENT OF THE OBJECTS

Therefore, it is an object of this invention to provide such a highly sensitive blood leak detector that not only permits prompt detection of very small traces of blood of a concentration as low as 0.001% but also operates stably over a long period of time.

It is another object of this invention to provide a blood leak detector which can accurately distinguish blood from bubbles often appearing in the cell.

A further object of this invention is to provide a blood leak detector having an alarm device which gives such an audibly distinguishable warning varying with the degree of the blood leak, thus permitting immediate sensing of the extent of danger without fear of failing to observe the meter panel even if an operator does not keep his eye upon the meter panel. Such overlooking in some cases might be fatal to a patient.

A still further object of this invention is to provide a dialysis system for artificial kidneys particularly suited for home use, in which blood supply to a dialyzer is cut off to prevent further leakage of blood when blood leak should happen, even if an operator is not at the bed side.

An even further object of this invention is to provide a blood leak detector convenient to handle whose operation and checking is made with ease, needing no sensitivity calibration based on actual use of a reference sample.

In a broader sense, it is an object of this invention to provide a circuit system for driving light-emitting elements at a constant brightness to permit a blood leak detector to operate stably.

It is a further object of this invention in a broader sense to provide a circuit system for AC amplification of an output signal of a photoelectric device to achieve stable operation of a blood leak detector.

It is still a further object of this invention to provide a measurement cell having a certain configuration which prevents bubbles from remaining therein.

The above and further objects, novel features and advantages of this invention will be apparent from the following description and claims taken in connection with the accompanying drawings.

BRIEF DESCRIPTION OF THE DRAWINGS

FIG. 9 is another schematic side view of an optical portion of this invention when light flux of a wide cross-section is employed, FIGS. 10 and 11 are schematic side views of improved measurement cells of this invention, FIG. 12 is a schematic representation of a blood leak detector in accordance with this invention. The blood leak detector is coupled to an artificial kidney as an application thereof.

DETAILED DESCRIPTION OF THE INVENTION

Figure 1:
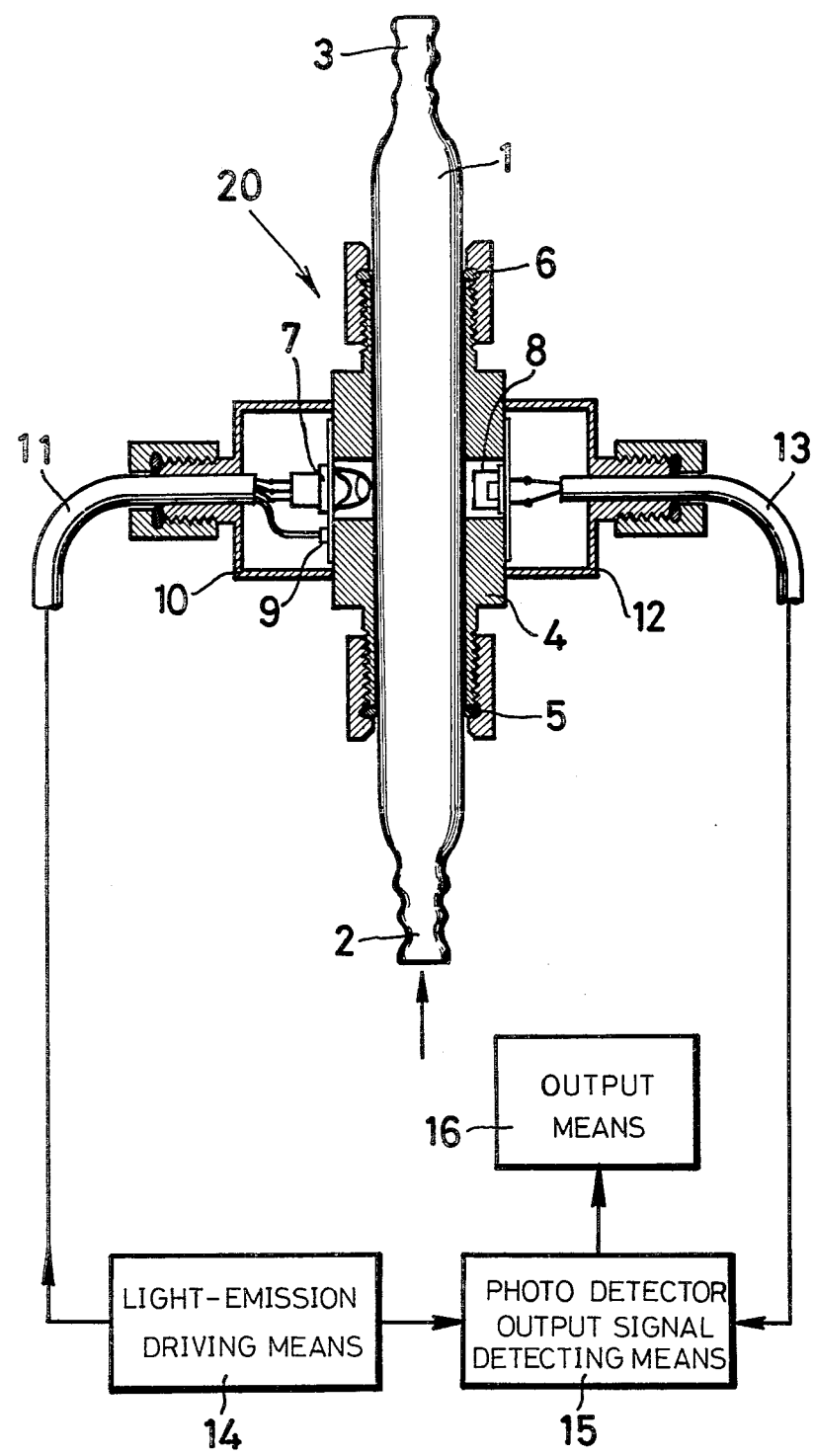
FIG. 1 is a vertical section of an optical portion coupled in circuit with a schematic block diagram of an electric circuit of a preferred embodiment of this invention.

Referring to FIG. 1, there is shown a measurement cell 1 formed from a cylinder or a square pillar tubular form made of transparent material such as "Pyrex" (a registered trademark of Corning Glass Works). Cell 1 has an inlet 2 at one end thereof through which a dialysis solution to be tested is introduced into the cell and an outlet 3 at the other end thereof through which the dialysis solution, having been tested, goes out. The central main part of the cell 1 constitutes a photometric portion 20, the detail of which will be described below. At the central part of the cell 1, a holder 4 made of opaque material such as metals and rubber is mounted, both ends of which are sealed with O-ring packings 5, 6. A part of the holder 4 is bored to a load pair of composite type light-emitting diodes 7 coupled with a condensing lens. A photo diode 8 is loaded so as to measure the light emitted by the diodes 7 and transmitted through the cell. A thermistor 9 is mounted in the neighborhood of the light-emitting diodes 7. This construction is incorporated in a shielded box 10, out of which lead wires of the light-emitting diodes 7 and the thermistor 9 are connected to a cable 11. The photo diode 8 is similarly shielded in a box 12, its lead wire being drawn therefrom by a cable 13. The composite light-emitting diodes 7 comprise a first light-emitting diode $D_1$ and a second light-emitting diode $D_2$, each being electrically independently operated with different wavelength characteristic. The first light-emitting diode $D_1$ emits radiation mainly at wavelengths of 520–600 nm which is involved within the absorption range of blood pigment, and the second light emitting diode $D_2$ emits mainly at 600–750 nm, that is, at longer wavelengths than the first. The photo diode 8 has a wavelength characteristic capable of detecting the radiation from both the light-emitting diodes $D_1$ and $D_2$, and has dimensions smaller than the diameter of or the length transverse to the cell 1, preferably smaller than one fifth thereof. Experiments have proved that when the first and the second light-emitting diodes $D_1$ and $D_2$ emit radiation with peaks at 555 and 695 nm, respectively, and a measurement cell having a diameter of 8 mm are used, the photo detective area smaller than $2 \times 2$ mm$^2$ permits easy distinguishing of the blood from bubbles. However, an area larger than $8 \times 8$ mm$^2$ makes the discrimination therebetween difficult.

Light-emission driving means 14 alternately energizes the first and the second light-emitting diodes $D_1$, $D_2$, which are adjusted to emit light with the same light intensity when no blood exists in the cell. This means 14 also supplies a reference signal such as a square wave signal to a photo detector output signal detecting means 15.

The means 15 detects blood leak independently of the existence of bubbles by analyzing the information involved in the output signal waveform of the photo diode 8. When both the intensities of the light emitted by the two diodes and transmitted through the cell 1 are well balanced or in an equilibrium, the means 15 does not transmit a detecting signal to an output device which will be later described. It gives an output signal deflected in the positive direction in proportion to the extent of the blood leak if it has occurred to cause the unbalance between the intensities; the signal is at the negative direction in the case when bubbles exist in the cell, as explained hereinafter in more detail.

The output means 16 indicates the detecting signal of the photo detector output signal detecting means 15 on an indicator or the like, and operates an alarm device when the amount of blood leak exceeds a predetermined level.

The above construction thus permits distinguishing blood from bubbles for the following reasons: the amount of light at longer wavelengths incident upon the photo diode 8 is relatively reduced when fine particles such as bubbles pass through the cell since the bubbles scatter the light at longer wavelengths remarkably. On the contrary to this, the smaller amount of light at shorter wavelengths enters the photo diode 8 when blood exists in the cell since the blood absorbs mainly at shorter wavelengths. As a consequence, there is a 180 degrees phase shift between the output signals in the two cases, which can be detected by phase detection.

Figure 2:
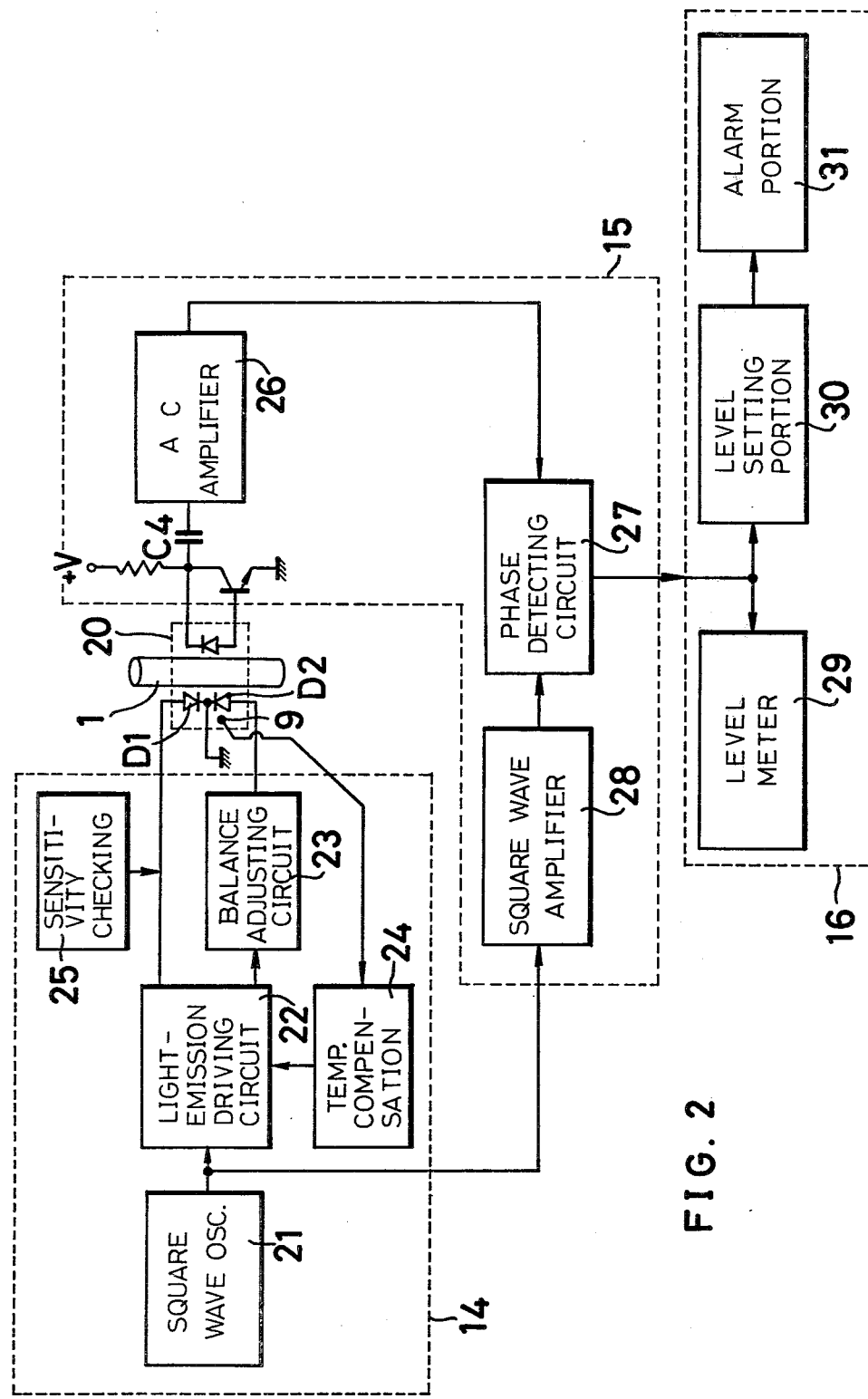
FIG. 2 is a detailed block diagram of an electric circuit of a preferred embodiment of this invention.

The details of the electric circuit means are represented in FIG. 1 as a block diagram, that is, the light-emission driving means 14, the photo detection output signal detecting means or transmitted signal detecting means 15 and the output means 16 will now be explained with reference to FIGS. 2, 3 and 4.

The light-emission driving means 14 comprises a square wave oscillator 21, a light-emission driving circuit 22, a balance adjusting circuit or portion 23, a temperature compensation circuit 24, and a sensitivity checking circuit 25. The square wave oscillator has a circuit configuration comprising an integrated circuit element $IC_1$, external resistances $R_1$, $R_2$, and a condenser $C_1$ (FIG. 3). It provides a reference signal in the form of a square wave, as illustrated in FIG. 5(A), which alternately energizes the two light-emitting diodes $D_1$, $D_2$, and also provides the reference square wave signal applied to the photo detection output signal detecting means 15 to detect the output signals. Usually the suitable period of the square wave for use ranges from 100 Hz to 100 KHz, which depends on the values of the resistances $R_1$, $R_2$ and the condenser $C_1$. In this preferred embodiment, 700 Hz is adopted with a 1:1 duty ratio which can be varied by the values of the resistances $R_1$, $R_2$. In the case when there is any difference between the brightness of the two light-emitting diodes $D_1$, $D_2$, if a large current is supplied to the diode with less brightness in a shorter time, and in turn a small current is supplied for a longer time to the the other diode with greater brightness, then the brightness of the diode with lesser brightness increases, keeping the balance therebetween, and consequently the sensitivity increases.

A light-emission driving portion 22 which comprises transistors $TR_1$, $TR_5$, $TR_6$, resistances $R_{12}$ to $R_{14}$, $R_{29}$, $R_{30}$, variable resistances $VR_4$, $VR_5$, and zener diodes $Z_1$, $Z_2$, is a circuit for alternately energizing the two light-emitting diodes $D_1$, $D_2$ at a constant current. When a square wave oscillator output voltage (A) is set at a high level (H level), a driving current is fed to the first light-emitting diode $D_1$ through the resistance $R_{13}$ and the transistor $TR_5$. On the other hand, a square wave oscillator output voltage at a low level (L level) causes the transistor $TR_1$ to conduct, and the second light-emitting diode $D_2$ is fed with driving current via the resistances $R_{14}$, $R_{30}$, the variable resistance $VR_3$, and the transistor $TR_6$ connected to the collector circuit of the transistor $TR_1$. Waveforms of the driving currents at the first and the second light-emitting diodes $D_1$ and $D_2$ are represented in FIGS. 5(B) and (C), respectively.

The balance adjusting portion 23 comprising the above mentioned variable resistance $VR_3$ adjusts the brightness of the second diode $D_2$ to keep the balance between the brightness of both the diodes so that the meter of the output device 16 reads zero when no blood leak is detected. The temperature compensating portion 24 comprising a heat sensitive element 9 such as a thermistor arranged in the proximity to the light-emitting diodes 7, and a variable resistance $VR_6$, has a function to vary the base voltage of the transistor $TR_6$ automatically with temperatures so that the brightness of the diodes 7 is kept constant.

The sensitivity checking circuit 25 is for checking the overall sensitivity of the optical and electric circuit system as well and includes a series circuit comprising a push button switch $S_4$ and a variable resistance $VR_7$ which are connected in parallel with the first light-emitting diode $D_1$, and temporarily causes the amount of light to vary in proportion to a predetermined level of blood leak. This sensitivity checking function permits not only to check both the optical and electric systems in a simple operation even if they vary with time, but also to adjust the sensitivity of the systems to the initial one by a variable resistance $VR_8$ of a phase detecting circuit 27 explained later, as the occasion arises.

Figure 3:
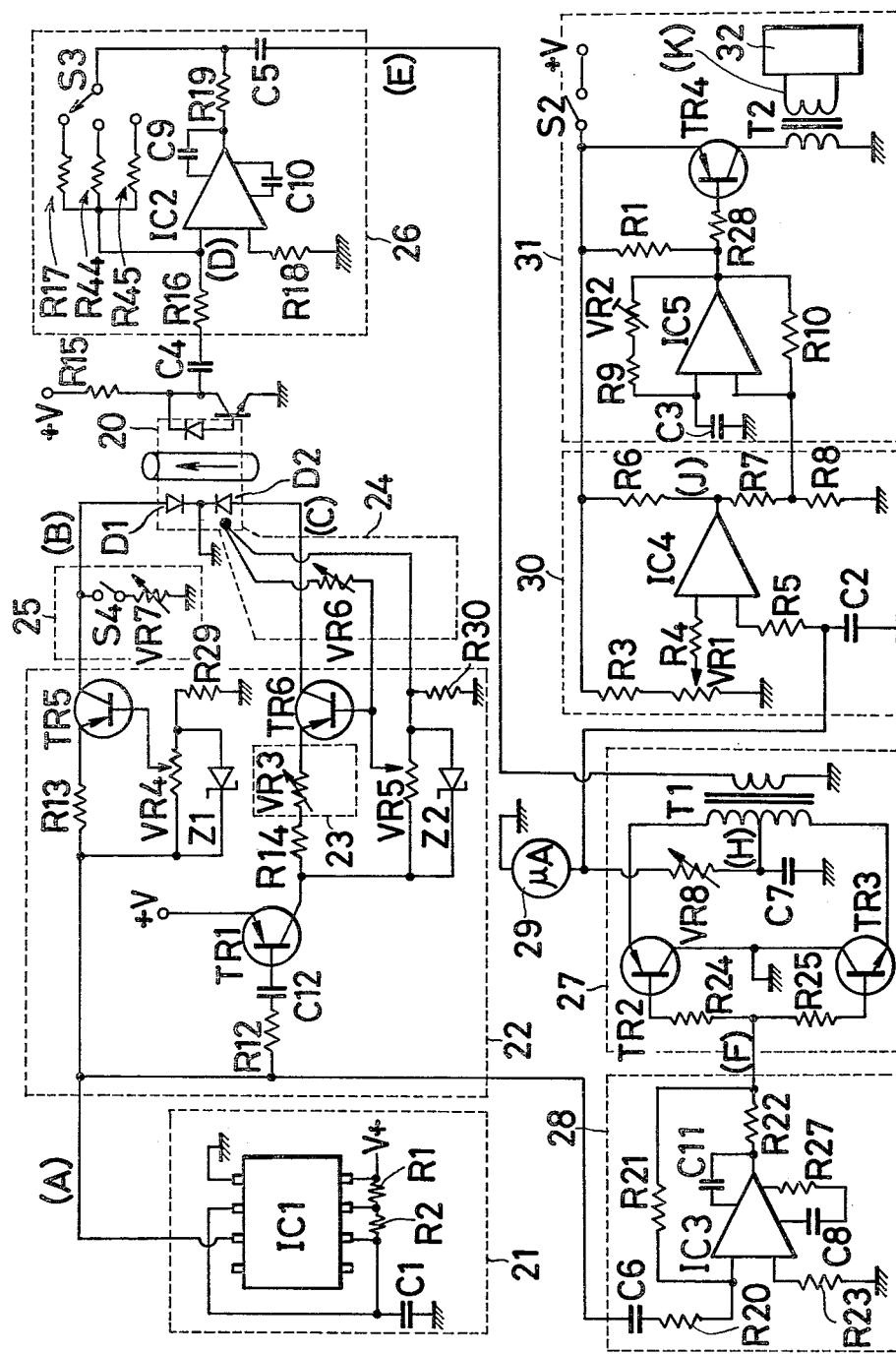
FIG. 3 is a circuit diagram corresponding to FIG. 2.
Figure 5:
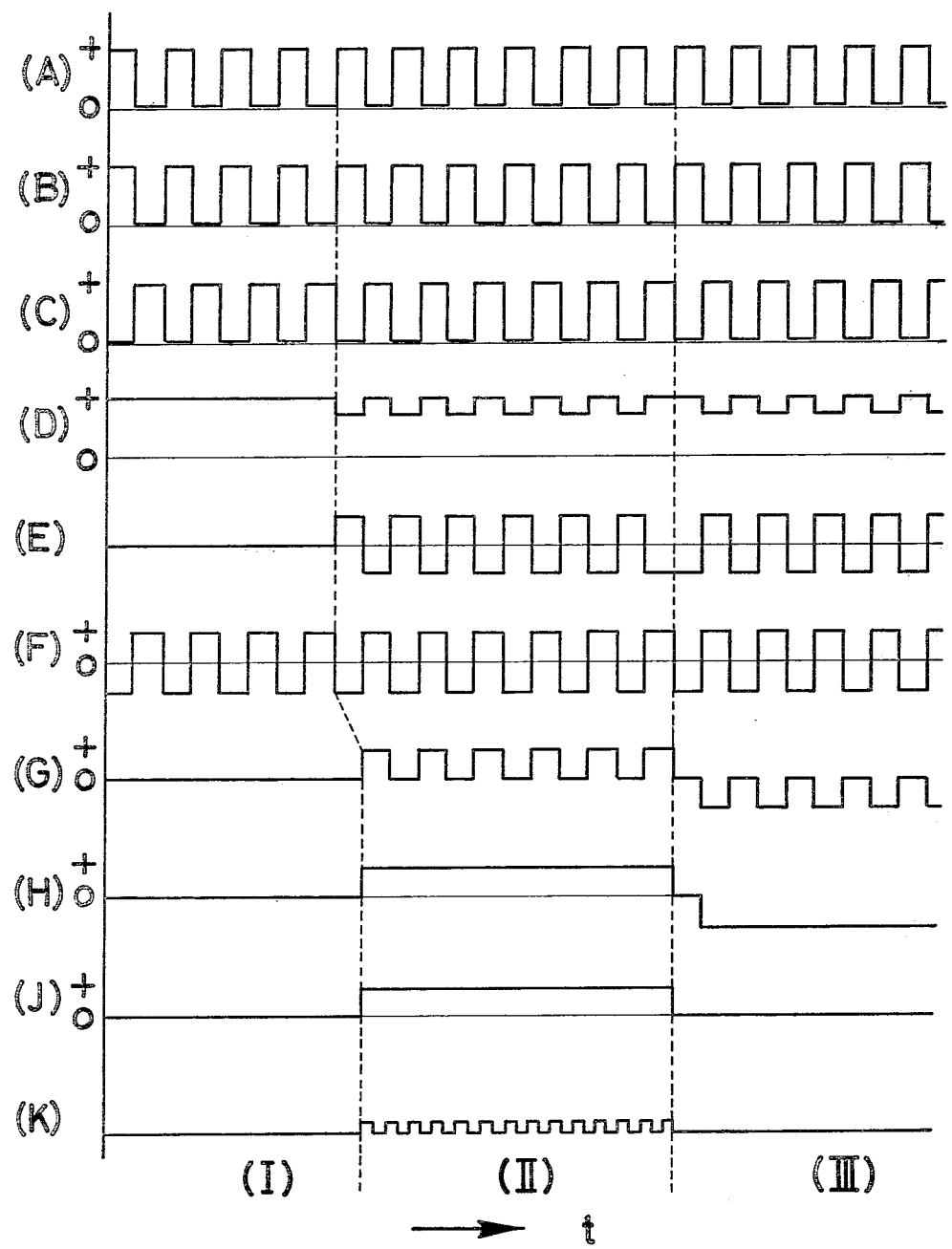
FIG. 5 is a time chart illustrating examples of function performed by the optical portion of FIG. 1 and the circuit diagram of FIG. 3, wherein (I) shows a normal case; (II) and (III) show the cases blood and bubbles exist in the cell, respectively. Alphabet letters in parenthesis from A to J except G and I refer to the positions where the signal is observed, respectively.

The photo detector output signal detecting means 15 comprises an AC amplifier 26, a phase detecting circuit 27, and a phase detection driving circuit or square wave amplifier 28, as shown in FIG. 3. The light transmitted through the measurement cell 1 enters into the photo diode 8 and is converted into an electric signal, which is in turn supplied via a condenser $C_4$ to an AC amplifier 26 as an input thereof. The waveform of a photo detecting output voltage after transmission through the condenser $C_4$ is shown in FIG. 5(D). No blood leak gives no square waveform in the photo detecting voltage as is illustrated in the mode (I) in FIG. 5. When blood leak has occurred, however, blood pigment absorbs at shorter wavelengths emitted by the first light-emitting diode $D_1$ to produce a square wave waveform on the photo detecting voltage as shown in the mode (II) in FIG. 5. Now this type of unbalance or disproportion is herein noted as a negative going waveform and called as deflection in the positive direction. On the other hand, when bubbles block the light path, the light at longer wavelenghts emitted by the second light-emitting diode $D_2$ is more distinctively prevented from transmitting through the cell, than at shorter wavelengths, thus producing a square wave as illustrated in the mode (III) in FIG. 5, 180° out of phase with the square wave produced by light absorption by the blood pigment. This type of unbalance is called herein as a positive going waveform or deflection in the negative direction. The AC amplifier 26 is a circuit device for high-gain amplification of the AC component, comprising an integrated circuit $IC_2$ which functions as an operational amplifier. The degree of amplification after choking the DC component with the condenser $C_4$ is chosen by a switch $S_3$. This AC amplifier 26 is preferably of a wide-band so as to follow closely up the high-speed modulated photo signals. An AC amplifier having a band width which varies from DC to 500 KHz is herein used. A waveform after the amplification of the AC component is shown in FIG. 5(E); the signal being then supplied to the phase detecting portion 27 via the condenser $C_5$.

The phase detecting portion 27 comprises a low-frequency transformer $T_1$ with a turn ratio of 1:1:1, switching transistors $TR_2$, $TR_3$ and others. The transistors $TR_2$ and $TR_3$ are caused to conduct alternately by an output voltage (F) from the square wave amplifier 28 which comprises an operational amplifier $IC_3$ to amplify an output signal (A) of the square wave oscillator 21. Consequently, when an input signal (E) is supplied to the primary winding of the transformer $T_1$, a phase detector output (H) of the input signal (E) referring to the square wave signal (F) appears at the middle point of the transformer $T_1$.

The output means 16 comprises a level meter 29, a blood leak detecting level set portion 30, and an alarm portion 31. The level meter 29 is a microammeter and is connected to an output terminal of the transformer $T_1$ through the variable resistance $VR_8$. A smoothing condenser $C_7$ is also connected to the output terminal of the transformer $T_1$. FIGS. 5(G) and (H) show waveforms of the phase detector output before and after smoothing, respectively. Thus, the level meter or indicator 29 remains at its zero reading in the mode (I) and it swings in the positive and negative directions corresponding to mode (II) and (III), respectively.

The blood leak detecting level set portion 30 in FIG. 3 is a sort of potential comparison circuit which by means of an operational amplifier $IC_4$ compares a reference input voltage which is set by a resistance $R_3$ and a variable resistance $VR_1$ with a voltage (H) received from the phase detecting portion 27. An output terminal voltage (J) of $IC_4$ goes to H level when the voltage (H) exceeds the reference input voltage. Therefore the $IC_4$ output terminal voltage (J) is at the L level in the mode (I) and (III), but at the H level only in the mode (II) when the blood pigment is detected.

The alarm portion 31 in FIG. 3 comprises a relaxation oscillation circuit or an astable multivibrator utilizing an operational amplifier $IC_5$, a switching transistor $TR_4$ and an alarm buzzer 32, giving a warning when the voltage (J) comes to the H level. A waveform of an output signal of the buzzer is illustrated in FIG. 5(K). The audio level of the warning is adjusted by a variable resistance $VR_2$. Alarm buzzer 32 is operative through transistor $TR_4$ and is connected through a power line having a switch $S_2$, which is opened to render the alarm portion 31 inoperative when alarming is not necessary.

Figure 6:
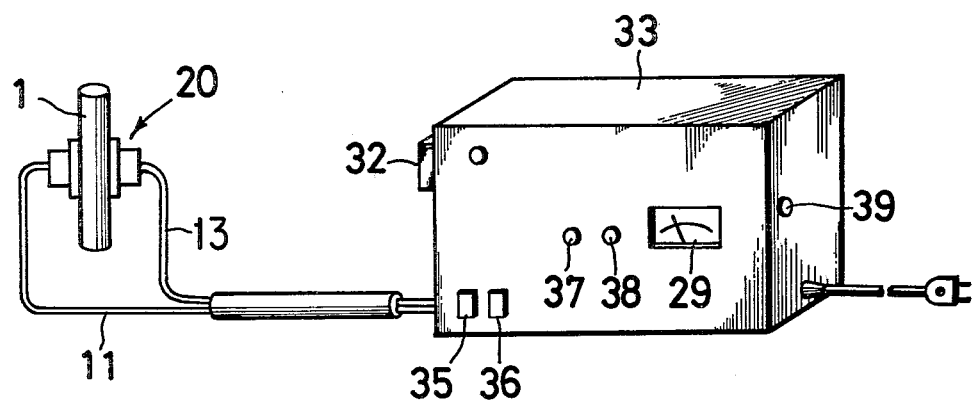
FIG. 6 is an example of a perspective view illustrating the exterior of a blood leak detector of this invention.
Figure 4:
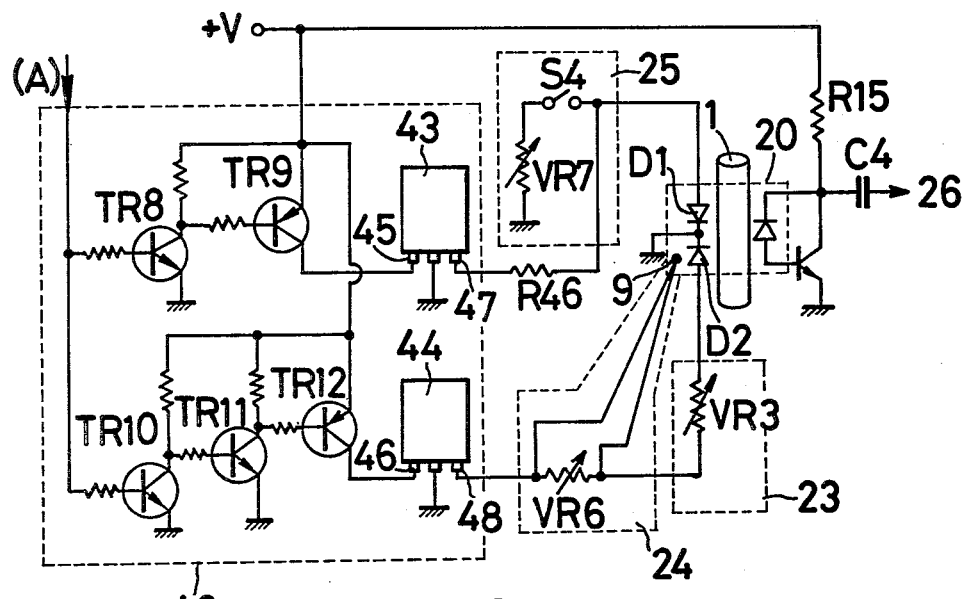
FIG. 4 is another circuit diagram of an emission driving circuit of FIG. 2.

FIG. 4 shows a circuit diagram of a light-emission driving circuit 42 driven by a driving system with a constant voltage. The circuit 42 can be replaced by a light-emission circuit 22 driven by a constant current driving system as shown in FIG. 3. The replacement gives more stabilized luminous brightness to the diodes $D_1$, $D_2$ which results in higher sensitivity. When a MC-7805 CP of Motorola is chosen for the constant voltage integrated circuit devices 43 and 44, for example, they have constant voltage input terminals of about 10 volts 45 and 46, respectively, and constant voltage output terminals of 5 volts 47 and 48, respectively. The output terminal voltages are kept constant regardless of fluctuation in the input voltage and temperatures therearound. Input voltages of the constant voltage integrated circuit devices 43 and 44 are supplied from the power line (+V) via switching transistors $TR_9$ and $TR_{12}$, respectively. A square wave signal (A) is applied to transistors $TR_8$ and a series of $TR_{10}$ and $TR_{11}$, respectively, to reverse the phase correspondingly. These transistors control a base current of the switching transistor $TR_9$ or $TR_{12}$. The other circuits except that above described are the same as those that are shown in FIG. 3, wherein each element is designated by like reference character. FIG. 6 shows a perspective view of the exterior of the device of this invention as an example; the housing 33 has the circuit devices therein already described by reference to FIGS. 2 and 3, and is connected through lead wires 11 and 13 to the photometric portion 20 which was described by reference to FIG. 1. The housing is also provided with a power switch 35, and an alarm switch 36 for controlling the switch $S_2$ of the alarm portion 31, the level meter or indicator 29, a knob 37 serving as a control for the variable resistance $VR_8$ for zero adjustment of the indicator 29, a knob 38 serving as a control for the variable resistance $VR_1$ used for setting the alarm level, and a push button 39 to control the switch $S_4$ for directing the sensitivity.

Table 1 shows the experimental results wherein 3 liters of sample liquids admixed therewith a predetermined amount of blood, bubbles, China ink and red ink, respectively, are tested by a detector according to this invention.

TABLE 1

| Additive | Amount Added (ml) | Meter Reading (Microammpere) |
|---|---|---|
| blood | 0.5 | +10 |
| blood | 0.05 | +1 |
| China ink | 0.5 | 0 |
| bubbles | — | ca. −1 |
| red ink | 0.5 | 0 |

As clearly seen, the meter reads about 10 microammperes in the positive direction when the sample contains blood as small as about 0.015%, but is deflected in the negative direction by bubbles. However, the meter scarcely swings when China or red ink is contained in the liquid. Thus, obstacles have the least influence upon the blood leak measurement. Furthermore, it has been found that the meter hardly drifts in the measurement for 48 hours under the experimental conditions. This enables one to assure the detecting limit of blood to be lower than 0.001%. When the constant current or voltage circuit portion was not directly connected to the light-emitting portion, and as the stability of the system depends merely on the stability of power line, then the meter drift reached as much as 10 microammperes in measurements for many hours, so that it was impossible to detect a low concentration of blood.

Figure 7:
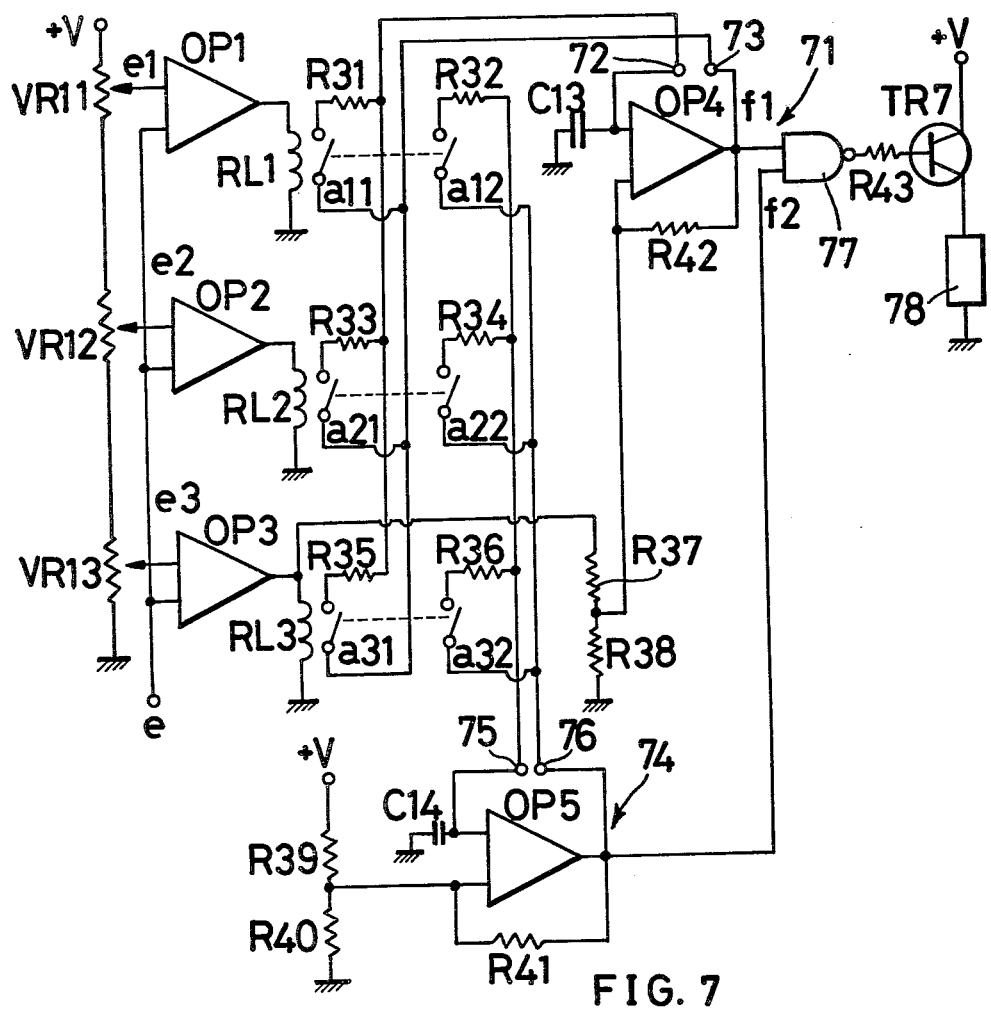
FIG. 7 is a circuit diagram of an alarm device in accordance with a preferred embodiment of this invention.
Figure 8:
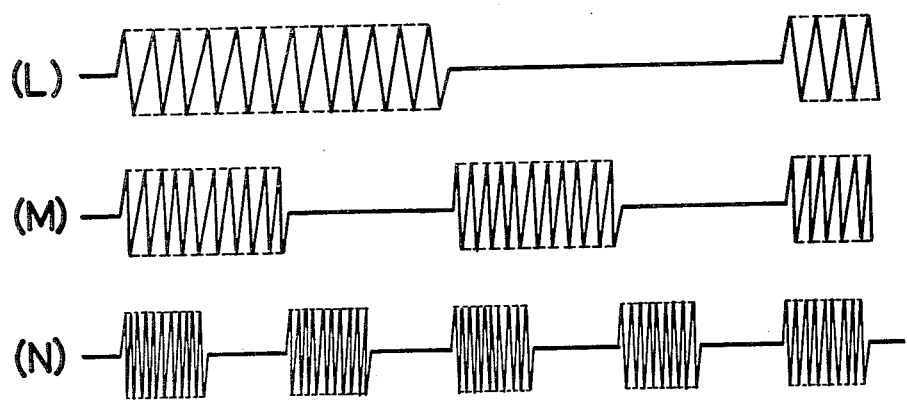
FIG. 8 is a waveform chart illustrating an example of the function of the circuit of FIG. 7, wherein L, M and N show different waveforms of audio alarm signals given according to the degree of blood leak, respectively.

FIG. 7 illustrates a circuit diagram of an alarm device embodying this invention, which gives such a warning as varies its tone or the like with the degree of blood leak detected. Reference voltages $e_1$, $e_2$ and $e_3$ of comparators $OP_1$, $OP_2$, and $OP_3$, respectively, where each comparator comprises an operational amplifier, are set at separate levels by variable resistances $VR_{11}$, $VR_{12}$ and $VR_{13}$, respectively. A phase detector output voltage e is commonly given to each comparator, each output terminal thereof being connected to relays $RL_1$, $RL_2$ and $RL_3$, respectively, each relay having at least a pair of 'a' contacts, $a_{11}$, and $a_{12}$, $a_{21}$ and $a_{22}$, $a_{31}$ and $a_{32}$, respectively. A free running multiple oscillator or an astable multivibrator 71 comprising an operational amplifier $OP_4$ generates square waves $f_1$ with different frequencies, such as, for example, 1.5 KHz, 1 KHz and 500 Hz, depending on which of the resistances $R_{31}$, $R_{33}$ and $R_{35}$ is connected between the terminals 72 and 73. Similarly, a free running multiple oscillator 74 including an operational amplifier $OP_5$ produces a long period square wave $f_2$ alternating between the H and L levels at intervals of 0.5, 1 or 2 seconds depending upon which of the resistances $R_{32}$, $R_{34}$ or $R_{36}$ is connected between the terminals 75 and 76. A NAND gate circuit 77 draws $f_1 \cdot f_2$, the logical product of $f_1$ and $f_2$, causing the alarm device 78 to be driven by a transistor $TR_7$. This alarm device 78 operates in such a manner that when an input voltage e is low, the comparator $OP_3$ works and causes the alarm device to give an undertone warning of 500 Hz at intervals of two seconds as shown in FIG. 8(L). On the other hand, a moderate input voltage over $e_2$ works the comparator $OP_2$ to give a medium-toned warning of 1 KHz every one second as shown in FIG. 8(M), and similarly a high input voltage over $e_3$ in turn works the comparator $OP_1$ to give rise to a shrill alarm of 1.5 KHz at intervals of half a second as shown in FIG. 8(N). Accordingly, the blood leak detector of this invention readily permits an operator to sense the extent of the blood leak without keeping his attention on the meter panel.

The above described alarm device utilizes a combination of an oscillation frequency varying system and an intermission period varying sound system, but it should be understood that either system can be sufficiently employed independently, and also such a system, for instance, in which two types of sounds having different frequencies are alternately given while varying the switching period thereof. It should be also understood that according to this invention the composite type light-emitting diodes 7 of the light-emitting portion can be replaced with a plurality of monochromatic diodes, each emitting at a separate wavelength. Or, filters which have the necessary wavelength characteristic can be put in front of a light-emitting element such as, for example, an incandescent bulb radiating in a broad range of wavelengths. In addition, instead of light-emitting diodes, other light-emitting elements such as lasers can be employed. Furthermore, the phase detecting driving portion can be omitted by the use of light-emitting diodes of both polarity as a light source, and the square wave generator can be replaced with a positive-negative pulse generator. In the meantime, in addition to the photo diodes previously described herein, various photo detecting elements such as photo transistors, photo tubes, CdS cells and the like can be used, of course. Such photo detecting elements, however, preferably have a response time of the order below $10^{-2}$ second, particularly below $10^{-3}$ second so as to recapitulate a reference square wave with high fidelity. It is desirable that they have limited or comparatively small photo detective areas so that the influence of scattered light is reduced. Such limitation or reduction of the photo detective areas can be achieved either by designing the elements themselves or by such means as irises.

When a light source of relatively great bulk 91 as shown in FIG. 9 and parallel light beams 92 of a large cross-section are used together having a photo detector 93 with a wide photo detective area, bubbles can still be distinguished to some extent if a Soller slit 94 is used, and if the surfaces thereof are black colored and have a spacing preferably less than 2 mm, is inserted parallel to the light path between the measurement cell 1 and the photo sensitive detecting portion 93.

According to this invention, measurement cells with an improved configuration are provided, and embodiments thereof are represented in FIGS. 10 and 11. As hereinbefore described, flowing bubbles can be accurately distinguished by the detector of this invention. However, when some of bubbles stick to the wall of the cell and block the light path, the amount of the transmitted light is decreased to lower the sensitivity of the detector. The improved measurement cells of this invention each have a wide cross-section at its dialysis solution entering portion 101, 111 usually defined by pressure and flowing amount of the solution, and the cells have a narrower cross-section at portion 102, 112 of about ½ to ⅓ of the cross-section of the entering portion, so that the light emmitted by the diodes pass through portions 102, 112. In other words, the measurement tube is narrowed to form a tapered portion 103, 113 at the front side at which the light path traverses the tube.

For example, when the inside diameter of the entering portion 101 or 111 and the inside diameter of the narrower portion 102 or 112 is 1.2 cm and 0.7 cm, respectively, and the flow rate is 500 ml per minute, then the dialysis solution flows at a rate of 7.35 cm a second at the wider, entering portion, and flows at a rate of 21.3 cm a second at the narrower portion. Thus, bubbles which flow into the cell are prevented from sticking to the wall of the narrower portion 102 or 112.

A schematic illustration of a blood leak detector of this invention is shown in FIG. 12 as incorporated into an artificial kidney.

A blood vessel of the human body 121 is connected to a dialyzer 122 of an artificial kidney through a switching valve means 123. The valve means 123 comprises a moving member 128 which can take a first state and a second state alternatively, the first state being a normal state where no blood leak exists and the second state being the state where blood leak has occurred. Valve means 123 also includes a fixed member 133 surrounding the member 128, and a switching member to switch over the respective state of the moving member 128. The fixed member 133 is provided with a first tube 124 for introducing blood before dialysis from the blood vessel into the dialyzer, a second tube 127 for returning the blood after dialysis to the blood vessel, a third tube 125 connected to a blood inlet of the dialyzer and a fourth tube 126 connected to a blood outlet of the dialyzer. The moving member 128 has at least two flow paths: a first flow path 129 and a second flow path 130. Thus, in the normal state where blood is normally dialyzed, the first flow path 129 interconnects the second tube 127 with the fourth tube 126 while the second flow path 130 interconnects the first tube 124 with the third tube 125. In the second state, however, which is produced by the blood leak signal, the first flow path 129 or the second path 130 interconnects the first tube 124 with the second tube 127. A rotary valve means as shown in the drawing permits switchover operation of the first state to the second by turning the moving member 90 degrees. This switchover operation can be achieved as well by a sliding switchover valve separately provided with first and second paths used in the first state, and a short path used in the second state. As previously described herein, the dialyzer 122 has the optical portion 20 detecting blood leak in the measurement cell, and the blood leak detecting device 131 gives an output signal to cause the moving member 128 to switchover from the first state to the second state. Accordingly when a blook leak should happen for one reason or another, the moving member 128 is automatically switched over so that the first tube 124, connected to the human body, and the second tube 127 are interconnected or shorted to prevent the blood from further leaking into the dialysis solution.

What we claim is:

1. Blood leak detector which comprises:
   a tubular measurement cell having at least a central part thereof which is transparent and having an inlet at one end thereof for a dialysis solution under test and an outlet at the other end thereof;
   light-emitting means for irradiating said measurement cell, comprising a first light-emitting element emitting mainly at wavelengths of 500–600 nm at which blood pigment absorbs light and a second light-emitting element emitting mainly at longer wavelengths than said first light-emitting element at wavelengths of 600 to 750 nm;
   photo detecting means for receiving the light transmitted through said measurement cell;
   means for alternately driving said first light-emitting element and the second light-emitting element and,
   means for discriminating among output signals of said photo detecting means, said driving means supplying a reference signal to said discriminating means for enabling thereof to discriminate between a first state wherein the amount of the transmitted light of said first light-emitting element is in equilibrium with that of said second light-emitting element, and a second state wherein the amount of the transmitted light of said first light-emitting element is smaller than that of said second light-emitting element.

2. Blood leak detector according to claim 1 which comprises: AC amplifying means to amplify an AC component of a photo detecting signal of photo detecting means; and phase discriminating means which is supplied with an emission switching signal as a reference input signal and with an output signal of the AC amplifying means as an input signal to be detected.

3. Blood leak detector according to claim 1 wherein a photo detecting area of photo detecting means has dimensions smaller than the length traverse to said measurement cell.

4. Blood leak detector according to claim 1 wherein said means for alternately driving said first light-emitting element and said second light-emitting element comprises:
   sealed constant voltage integrated circuit means having a constant output terminal and a power input terminal voltage;
   switching means having an input control line and a 2-terminal switching circuit which is cycled on and off by said input control line;
   circuit means to connect one of said lines of said switching circuit to a power line; circuit means to provide a square wave signal in the range of 100 Hz to 100 KHz to said input control line of said switching means;
   circuit means to connect the other line of said switching circuit to said constant voltage integrated circuit means; and,
   circuit means to connect either said first light-emitting element or said second light-emitting element to said constant voltage integrated circuit means.

5. Blood leak detector according to claim 1 wherein said measurement cell has a tapered portion to reduce the cross-section thereof between said inlet for dialysis solution and a light path crossing said measurement cell.

6. Blood leak detector according to claim 1 which additionally comprises: push button switch means connected to circuit means permitting either to reduce luminous intensity of a first light-emitting diode or to increase luminous intensity of a second light-emitting diode and causing unbalance electrically between photo detector outputs; and a sensitivity checking system indicating a predetermined level of blood leak by operating the push button switch means without using reference samples.

7. Blood leak detector according to claim 1 which additionally comprises:

alarm means to provide an audibly distinguishable warning responsive to at least one of the factors of frequency, amplitude and intermission, which varies in accordance with the strength of a blood leak output signal.

8. Artificial kidney dialysis system which comprises: a blood leak detector according to claim 1, a first tube to introduce blood before dialysis into a dialyzer; a second tube to introduce blood after dialysis into a blood vessel; a third tube connected to a blood inlet of the dialyzer; a fourth tube connected to a blood outlet of the dialyzer; flow path means capable of being switched over between a first state in which the first tube is interconnected to the third tube and the second tube is interconnected to the fourth tube, and a second state in which the first tube in interconnected to the second tube; and state switching over means to switch over the flow path means from the first state to the second state on detecting the output signal of the blood leak detector, whereby when a blood leak signal is produced, the first tube, to introduce blood before dialysis into the dialyzer, is interconnected to the second tube to introduce blood after dialysis into the blood vessel, to prevent the blood from entering the dialyzer.

9. Blood leak detector which comprises: a transparent measurement cell through which dialysis solution under test flows; composite light-emitting diodes irradiating the measurement cell and having a first light-emitting diode which emits in the range of 520–600 nm and a second light-emitting diode which emits in the range of 600–750 nm; a photo detecting element to receive the light from the light emitting diodes transmitted through the measurement cell; means for driving the first light-emitting diode and the second light-emitting diode alternatively after a reference square wave signal; means for adjusting the balance between an output signal of a photo detecting element due to the first light-emitting diode and an output signal of the photo detecting element due to the second light-emitting diode in the normal state in which no blood leak exists; and means for detecting deflection from the normal state resulting from change either of the output signal of the photo detecting element due to the first light-emitting diode or of the output signal of the photodetecting element due to the second light-emitting diode.

10. Blood leak detector according to claim 9 wherein said reference square wave signal is used to cause a difference in the duration of the emitting time between said first and said second light-emitting diode.

11. Blood leak detector according to claim 9 which additionally comprises: a first driving circuit and a second driving circuit for energizing alternately a first light-emitting diode and a second light-emitting diode; and a thermal sensitive element connected either to the first driving circuit or to the second driving circuit and positioned in proximity to the diodes so as to compensate automatically the change of the intensities of the first light-emitting diode and the second light-emitting diode due to temperature change.

* * * * *